(12) United States Patent
Richard et al.

(10) Patent No.: US 10,612,059 B2
(45) Date of Patent: Apr. 7, 2020

(54) METHODS AND COMPOSITIONS FOR THE TREATMENT OF CELLULOSIC BIOMASS AND PRODUCTS PRODUCED THEREBY

(71) Applicant: Comet Biorefining Inc., Sarnia, Ontario (CA)

(72) Inventors: Andrew Richard, London (CA); Dennis D'Agostino, Waterdown (CA)

(73) Assignee: Comet Biorefining Inc., Sarnia, Ontario (CA)

( * ) Notice: Subject to any disclaimer, the term of this patent is extended or adjusted under 35 U.S.C. 154(b) by 0 days.

(21) Appl. No.: 15/565,069

(22) PCT Filed: Apr. 8, 2016

(86) PCT No.: PCT/CA2016/050402
§ 371 (c)(1),
(2) Date: Oct. 6, 2017

(87) PCT Pub. No.: WO2016/161515
PCT Pub. Date: Oct. 13, 2016

(65) Prior Publication Data
US 2018/0119188 A1    May 3, 2018

Related U.S. Application Data (60) Provisional application No. 62/145,785, filed on Apr. 10, 2015, provisional application No. 62/246,271, filed on Oct. 26, 2015.

(51) Int. Cl.
| | | |
|---|---|---|
| C12P 19/02 | (2006.01) |
| C12P 19/14 | (2006.01) |
| D21C 5/00 | (2006.01) |
| C12N 9/96 | (2006.01) |
| C13K 1/02 | (2006.01) |
| C13K 11/00 | (2006.01) |
| C12N 9/42 | (2006.01) |
| D21C 1/10 | (2006.01) |
| C13K 1/04 | (2006.01) |
| C08B 15/08 | (2006.01) |

(52) U.S. Cl.
CPC ............ *C12P 19/02* (2013.01); *C12N 9/2437* (2013.01); *C12N 9/96* (2013.01); *C12P 19/14* (2013.01); *C12Y 302/01004* (2013.01); *C13K 1/02* (2013.01); *C13K 1/04* (2013.01); *C13K 11/00* (2013.01); *D21C 1/10* (2013.01); *D21C 5/005* (2013.01); *C08B 15/08* (2013.01); *C12P 2201/00* (2013.01)

(58) Field of Classification Search
CPC ........... C12P 19/02; C12P 19/04; C12P 19/14; C12P 2201/00; C12P 2203/00
See application file for complete search history.

(56) References Cited

U.S. PATENT DOCUMENTS

| | | | |
|---|---|---|---|
| 4,025,389 A | 5/1977 | Poulsen | |
| 5,902,782 A | 5/1999 | Hall et al. | |
| 5,967,157 A * | 10/1999 | Chatterjee ............ | C11D 3/0026 134/25.2 |
| 6,090,595 A | 7/2000 | Foody et al. | |
| 6,632,448 B2 | 10/2003 | Tanaka et al. | |
| 6,692,578 B2 | 2/2004 | Schmidt et al. | |
| 7,427,643 B2 | 9/2008 | Gatenholm et al. | |
| 7,449,209 B2 | 11/2008 | Dreese et al. | |
| 7,670,678 B2 | 3/2010 | Phan | |
| 7,709,033 B2 | 5/2010 | Kvist et al. | |
| 7,807,419 B2 | 10/2010 | Hennessey et al. | |
| 7,998,713 B2 | 8/2011 | Dunson, Jr. et al. | |
| 8,017,820 B2 | 9/2011 | Foody et al. | |
| 8,022,260 B2 | 9/2011 | O'Connor et al. | |
| 8,148,495 B2 | 4/2012 | Harris et al. | |
| 8,211,483 B2 | 7/2012 | Lee et al. | |
| 8,227,448 B2 | 7/2012 | Van Laere et al. | |
| 8,318,458 B2 | 11/2012 | Harris et al. | |
| 8,460,898 B2 | 6/2013 | Diner et al. | |
| 8,465,788 B2 | 6/2013 | Ekhart et al. | |
| 8,623,402 B2 | 1/2014 | Delcour | |
| 8,658,405 B2 | 2/2014 | Johal et al. | |
| 8,685,690 B2 | 4/2014 | Yang et al. | |
| 8,741,376 B2 | 6/2014 | Broekaert et al. | |
| 8,778,639 B1 | 7/2014 | Spodsberg | |
| 8,809,033 B2 | 8/2014 | Sweeney et al. | |

(Continued)

FOREIGN PATENT DOCUMENTS

| | | |
|---|---|---|
| CA | 1175820 A | 10/1984 |
| CA | 2615904 A1 | 2/1994 |

(Continued)

OTHER PUBLICATIONS

International Search Report and Written Opinion, PCT/CA2016/050402, dated Aug. 11, 2016.
Extended European Search Report received for EP16775983, dated Dec. 6, 2018, 8 pages.
Alkasrawi, et al. (2003) "The effect of Tween-20 on simultaneous saccharification and fermentation of softwood to ethanol", Enyme and Microbial Technology 33:71-78.
Bensah and Mensah (2013) "Chemical Pretreatment Methods for the Production of Cellulosic Ethanol: Technologies and Innovations", International Journal of Chemical Engineering, 21 pages.

(Continued)

*Primary Examiner* — Rebecca E Prouty
(74) *Attorney, Agent, or Firm* — Fish & Richardson P.C.

(57) ABSTRACT

A two-step method for activating a cellulosic feedstock is described. The feedstock is subjected to a first high temperature activation step at a temperature greater than 190° C. and a second activation step at a lower temperature under alkali conditions. Also described are methods and compositions for the enzymatic hydrolysis of activated cellulose using one or more cellulase enzymes, a surfactant and polyaspartic acid. Also described are products of the methods.

26 Claims, 1 Drawing Sheet

(56) References Cited

U.S. PATENT DOCUMENTS

| | | |
|---|---|---|
| 8,815,561 B2 | 8/2014 | Liu et al. |
| 8,877,474 B2 | 11/2014 | Yang et al. |
| 8,894,771 B2 | 11/2014 | Floyd et al. |
| 8,927,038 B2 | 1/2015 | Broekaert et al. |
| 8,962,288 B2 | 2/2015 | Quinlan et al. |
| 9,061,046 B2 | 6/2015 | Broekaert et al. |
| 9,080,165 B2 | 7/2015 | Fidantsef et al. |
| 9,109,213 B2 | 8/2015 | Schooneveld-Bergmans et al. |
| 9,121,013 B2 | 9/2015 | Schooneveld-Bergmans et al. |
| 9,150,936 B2 | 10/2015 | Dottori et al. |
| 9,163,223 B2 | 10/2015 | Schooneveld-Bergmans et al. |
| 9,175,050 B2 | 11/2015 | Schooneveld-Bergmans et al. |
| 9,175,277 B2 | 11/2015 | McBrayer et al. |
| 9,193,982 B2 | 11/2015 | Sjoede et al. |
| 9,260,704 B2 | 2/2016 | Schooneveld-Bergmans et al. |
| 9,303,074 B2 | 4/2016 | Schnorr et al. |
| 9,353,363 B2 | 5/2016 | Lange et al. |
| 9,365,843 B2 | 6/2016 | Zhang et al. |
| 9,370,193 B2 | 6/2016 | Sorensen et al. |
| 9,410,136 B2 | 8/2016 | Schnorr et al. |
| 9,428,772 B2 | 8/2016 | Hamrick |
| 9,434,788 B2 | 9/2016 | Yadav et al. |
| 9,441,214 B2 | 9/2016 | Schooneveld-Bergmans et al. |
| 9,506,049 B2 | 11/2016 | Tang et al. |
| 9,624,481 B2 | 4/2017 | Liu et al. |
| 9,677,060 B2 | 6/2017 | Johansen et al. |
| 9,689,011 B2 | 6/2017 | Ellegård et al. |
| 9,695,433 B2 | 7/2017 | Zhang et al. |
| 9,738,881 B2 | 8/2017 | Los et al. |
| 9,752,168 B2 | 9/2017 | Quinlan et al. |
| 9,752,169 B2 | 9/2017 | Cotti Comettini et al. |
| 9,765,373 B2 | 9/2017 | Schnorr et al. |
| 9,771,568 B2 | 9/2017 | Liu et al. |
| 9,783,860 B2 | 10/2017 | Floyd et al. |
| 9,790,530 B2 | 10/2017 | Shaghasi et al. |
| 9,795,628 B2 | 10/2017 | Hageman |
| 9,797,021 B2 | 10/2017 | Floyd et al. |
| 9,848,626 B2 | 12/2017 | Shen et al. |
| 9,879,294 B2 | 1/2018 | Huang et al. |
| 9,896,707 B2 | 2/2018 | Thompson et al. |
| 9,932,414 B2 | 4/2018 | Quinlan et al. |
| 9,957,491 B2 | 5/2018 | Zhang et al. |
| 9,963,725 B2 | 5/2018 | Lali et al. |
| 9,994,833 B2 | 6/2018 | Liu et al. |
| 10,041,136 B2 | 8/2018 | St. John et al. |
| 10,174,351 B2 | 1/2019 | Smits et al. |
| 10,190,103 B2 | 1/2019 | Börjesson et al. |
| 10,207,197 B2 | 2/2019 | Mitchell |
| 10,308,921 B2 | 6/2019 | Tang et al. |
| 2005/0209122 A1 | 9/2005 | Jorgensen et al. |
| 2008/0227166 A1 | 9/2008 | Allain et al. |
| 2009/0056889 A1 | 3/2009 | Ren et al. |
| 2010/0298611 A1 | 11/2010 | Parekh et al. |
| 2011/0020873 A1 | 1/2011 | Ren et al. |
| 2011/0111456 A1 | 5/2011 | Medoff |
| 2011/0159554 A1 | 6/2011 | Takahashi et al. |
| 2011/0250645 A1 | 10/2011 | Schiffino et al. |
| 2011/0300586 A1 | 12/2011 | Liu et al. |
| 2012/0111514 A1 | 5/2012 | Dottori et al. |
| 2012/0240921 A1 | 9/2012 | Fukuoka et al. |
| 2013/0004994 A1 | 1/2013 | Hanakawa et al. |
| 2013/0005952 A1 | 1/2013 | Belanger et al. |
| 2013/0029406 A1 | 1/2013 | Dottori et al. |
| 2013/0052713 A1 | 2/2013 | Yang et al. |
| 2013/0059345 A1* | 3/2013 | Kurihara .............. C12P 19/14 435/99 |
| 2013/0244293 A1 | 9/2013 | Balan et al. |
| 2013/0261340 A1 | 10/2013 | Medoff |
| 2014/0038244 A1 | 2/2014 | Chesonis et al. |
| 2014/0093918 A1 | 4/2014 | Zhang et al. |
| 2014/0106418 A1 | 4/2014 | Parekh et al. |
| 2015/0307952 A1 | 10/2015 | Saville |
| 2017/0369517 A1 | 12/2017 | Shekiro, III et al. |

FOREIGN PATENT DOCUMENTS

| | | |
|---|---|---|
| CA | 2179970 A1 | 12/1996 |
| CA | 2189899 C | 5/1997 |
| CA | 2240035 A1 | 12/1998 |
| CA | 2282094 A1 | 4/2000 |
| CA | 2368872 A1 | 10/2000 |
| CA | 2373936 | 1/2001 |
| CA | 2400336 A1 | 8/2001 |
| CA | 2418726 C | 2/2002 |
| CA | 2420064 A1 | 2/2002 |
| CA | 2477196 A1 | 8/2003 |
| CA | 2583256 A1 | 3/2006 |
| CA | 2580226 A1 | 4/2006 |
| CA | 2580228 A1 | 4/2006 |
| CA | 2535246 | 8/2006 |
| CA | 2535246 A1 | 8/2006 |
| CA | 2603645 A1 | 10/2006 |
| CA | 2831082 A1 | 1/2007 |
| CA | 2655035 A1 | 12/2007 |
| CA | 2595484 A1 | 2/2008 |
| CA | 2565433 A1 | 4/2008 |
| CA | 2576317 A1 | 7/2008 |
| CA | 2674534 A1 | 7/2008 |
| CA | 2684007 A1 | 10/2008 |
| CA | 2685177 A1 | 11/2008 |
| CA | 2691524 A1 | 12/2008 |
| CA | 2694245 A1 | 1/2009 |
| CA | 2694875 A1 | 2/2009 |
| CA | 2697962 A1 | 2/2009 |
| CA | 2698641 A1 | 3/2009 |
| CA | 2701862 A1 | 4/2009 |
| CA | 2701949 A1 | 4/2009 |
| CA | 2703085 A1 | 5/2009 |
| CA | 2720177 A1 | 10/2009 |
| CA | 2731983 | 2/2010 |
| CA | 2731350 A1 | 3/2010 |
| CA | 2739451 A1 | 4/2010 |
| CA | 2739704 A1 | 5/2010 |
| CA | 2739709 A1 | 5/2010 |
| CA | 2746783 A1 | 6/2010 |
| CA | 2738886 A1 | 7/2010 |
| CA | 2745508 A1 | 7/2010 |
| CA | 2715458 C | 10/2010 |
| CA | 2714946 C | 12/2010 |
| CA | 2763588 A1 | 12/2010 |
| CA | 2673134 A1 | 1/2011 |
| CA | 2714937 A1 | 1/2011 |
| CA | 2767290 A1 | 1/2011 |
| CA | 2789199 A1 | 1/2011 |
| CA | 2771147 | 2/2011 |
| CA | 2772112 A1 | 3/2011 |
| CA | 2772115 A1 | 3/2011 |
| CA | 2775355 A1 | 4/2011 |
| CA | 2775656 A1 | 4/2011 |
| CA | 2783794 A1 | 6/2011 |
| CA | 2784105 A1 | 6/2011 |
| CA | 2783201 A1 | 7/2011 |
| CA | 2786949 A1 | 8/2011 |
| CA | 2786951 A1 | 8/2011 |
| CA | 2788548 A1 | 8/2011 |
| CA | 2695823 A1 | 9/2011 |
| CA | 2795503 A1 | 9/2011 |
| CA | 2800996 A1 | 12/2011 |
| CA | 2804662 A1 | 1/2012 |
| CA | 2806130 A1 | 2/2012 |
| CA | 2806132 A1 | 2/2012 |
| CA | 2802221 A1 | 3/2012 |
| CA | 2809519 A1 | 3/2012 |
| CA | 2810455 A1 | 4/2012 |
| CA | 2811681 A1 | 4/2012 |
| CA | 2818175 | 6/2012 |
| CA | 2838560 A1 | 1/2013 |
| CA | 2842781 A1 | 1/2013 |
| CA | 2873106 A1 | 11/2013 |
| CA | 2820210 A1 | 12/2013 |
| CA | 2900759 A1 | 9/2014 |
| CA | 2818759 A1 | 5/2015 |
| EP | 1758470 | 7/2008 |

(56) References Cited

FOREIGN PATENT DOCUMENTS

| | | |
|---|---|---|
| EP | 1675481 | 11/2008 |
| EP | 2323669 | 5/2015 |
| EP | 2313514 | 11/2016 |
| EP | 2621503 | 11/2017 |
| EP | 2117322 | 10/2018 |
| EP | 2648540 | 10/2018 |
| EP | 3157340 | 12/2018 |
| JP | H10-316999 | 2/1998 |
| JP | 2002-171960 | 6/2002 |
| WO | 1994/029424 A1 | 12/1994 |
| WO | 1995/20065 A1 | 7/1995 |
| WO | WO1995/020065 | 7/1995 |
| WO | 2001/030855 A1 | 5/2001 |
| WO | WO 2006/027529 | 3/2006 |
| WO | 2010/071805 A2 | 6/2010 |
| WO | 2011/046816 A1 | 4/2011 |
| WO | WO 2011/115039 | 9/2011 |
| WO | 2012/040003 A2 | 3/2012 |
| WO | 2013/040702 A1 | 3/2013 |
| WO | WO 2013/071883 | 5/2013 |
| WO | WO 2013/101650 | 7/2013 |
| WO | 2013/117823 A1 | 8/2013 |
| WO | 2013/131015 A1 | 9/2013 |
| WO | 2013/163571 A2 | 10/2013 |
| WO | 2013/164234 A1 | 11/2013 |
| WO | WO 2013/171100 | 11/2013 |
| WO | 2014/026154 A1 | 2/2014 |
| WO | 2014/031667 A1 | 2/2014 |
| WO | 2014/110223 A1 | 7/2014 |
| WO | WO 2014/119990 | 8/2014 |
| WO | 2014/144588 A1 | 9/2014 |
| WO | WO 2014/147393 | 9/2014 |
| WO | 2015/016930 A1 | 2/2015 |
| WO | WO 2015/016930 | 2/2015 |
| WO | WO 2015/040159 | 3/2015 |
| WO | 2015/050881 A1 | 4/2015 |
| WO | 2015/063549 A1 | 5/2015 |
| WO | 2015/086782 A1 | 6/2015 |
| WO | 2015/086783 A1 | 6/2015 |
| WO | 2015/104460 A1 | 7/2015 |
| WO | 2015/107413 A1 | 7/2015 |
| WO | WO 2015/176173 | 11/2015 |
| WO | WO 2016/045569 | 3/2016 |
| WO | WO2016/161515 | 10/2016 |
| WO | WO 2017/147163 | 8/2017 |

OTHER PUBLICATIONS

Brethauer, et al. (2011) "The effect of bovine serum albumin on batch and continuous enzymatic cellulose hydrolysis mixed by stirring or shaking", Bioresource Technology, 4 pages.

Dekker and Wallis (1983) "Enzymic Saccharification of Sugarcane Bagasse Pretreated by Autohydrolysis—Steam Explosion" Biotechnology and Bioengineering, 25:3027-3048.

Harris, et al. (1984) "Two-Stage, Dilute Sulfuric Acid Hydrolysis of Hardwood for Ethanol Production" Energy Research, Development, and Application, Forest Products Laboratory, Forest Service, USDA, Madison, Wisconsin 53705, 20 pages.

Kaya, et al. (1995) "Influence of surfactants on the enzymatic hydrolysis of xylan and cellulose", Tappi Journal, 78 (10)150-157.

Tjerneld, et al. (1985) "Enzymatic Hydrolysis of Cellulose in Aqueous Two-Phase Systems. II. Semicontinuous Conversion of a Model Substrate, Solka Floc BW 200", Biotechnology and Bioengineering 27:1044-1050.

Tu, et al. (2009) "The potential of enzyme recycling during the hydrolysis of a mixed softwood feedstock", Bioresource Technology 100:6407-6415.

Wang (2008) "Cellulose Fiber Dissolution in Sodium Hydroxide Solution at Low Temperature: Dissolution Kinetics and Solubility Improvement", Georgia Institute of Technology; 2008, 148 pages.

Cheng et al, "Separation, Purification and Characterization of Corn Stover Hemicelluloses," Cellulose Chemistry and Technology, 2017, 51:215-222.

Egüés et al, "Effect of alkaline and autohydrolysis processes on the purity of obtained hemicelluloses from corn stalks," Bioresource Technology, 2012, 103:239-248.

Francois et al, "Tolerance and the effect of high doses of wheat bran extract, containing arabinoxylan-oligosaccharides, and oligofructose on faecal output: a double-blind, randomised, placebo-controlled, cross-over trial," Journal of Nutritional Science, 12 pages, 2014.

Lu et al, "Arabinoxylan fiber, a byproduct of wheat flour processing, reduces the postprandial glucose response in normoglycemic subjects," Am. J. Clin. Nutr., 2000, 71:1123-1128.

Magaletta et al, "In vitro method for predicting glycemic index of foods using simulated digestion and an artificial neural network," Cereal Chemistry, 2015, 87.

Malunga & Beta, "Antioxidant Capacity of Water-Extractable Arabinoxylan from Commercial Barley, Wheat, and Wheat Fractions," Cereal Chem., 2015, 92:(1):29-36.

Perez and Samain, "Structure and Engineering of Cellulose" Advances in Carbohydrate Chemistry and Biochemistry, vol. 64, Elsevier (2010).

Sun et al, "Physico-chemical and structural characterization of hemicelluloses from wheat straw by alkaline peroxide extraction," Polymer, 41:2647-2656, 2000.

Belafi-Bako et al., "Continuous enzymatic cellulose hydrolysis in a tubular membrane bioreactor," Enzyme and Microbial Technology, 38(1-2):155-161, Jan. 2006.

Ding et al., "Enzymatic conversion of cellulosic materials in a continuous stirred take reactor with an ultrafiltration membrane," Food for Health in the Pacific Rim: 3rd International Conference of Food Science and Technology. Trumbull, Connecticut, USA: Food & Nutrition Press, Inc., pp. 433-445, Dec. 2004.

Ghose et al., "A model for continuous enzymatic saccharification of cellulose with simultaneous removal of glucose syrup," Biotechnol. Bioeng., 12(6):921-946, Nov. 1970.

Hodge et al., "Model-based fed-batch for high-solids enzymatic cellulose hydrolysis," Appl. Biochem. Biotechnol., 152(1):88-107, Jan. 2009.

Mandels et al., "The use of adsorbed cellulase in the continuous conversion of cellulose to glucose," J. Polymer Sci., 36(1):445-459, 1971.

Tanaka et al., "Removal of lignin and reuse of cellulases for continuous saccharification of lignocelluloses," Biotechnol. Bioeng., 32(7):897-902, Sep. 1988.

Yang et al., "Aqueous extraction of corncob xylan and production of xylooligosaccharides," LWT-Food Science and Technology, 38(6):677-82, Sep. 2005.

Eckard et al., "Enzyme recycling in a simultaneous and separate saccharification and fermentation of corn stover: A comparison between the effect of polymeric micelles of surfactants and polypeptides," Bioresour. Technol., 132:202-9, Mar. 2013.

\* cited by examiner

10,612,059 B2

METHODS AND COMPOSITIONS FOR THE TREATMENT OF CELLULOSIC BIOMASS AND PRODUCTS PRODUCED THEREBY

CROSS REFERENCE TO PRIOR APPLICATIONS

This application is a National Stage Application of PCT/CA2016/050402 filed Apr. 8, 2016, which claims benefit of U.S. Application No. 62/145,785, filed Apr. 10, 2015, and claims the benefit of U.S Application No. 62/246,271, filed Oct. 26, 2015, all of which are incorporated herein by reference. To the extent appropriate, a claim of priority is made to each of the above disclosed applications.

FIELD

This application relates to methods for treating cellulosic biomass to produce cellulosic sugars. In one aspect, methods for activating cellulosic feedstock and/or enzymatic hydrolysis to produce glucose are provided. Activated cellulosic feedstock and products produced from enzymatic hydrolysis of the activated cellulosic feedstock are also provided.

INTRODUCTION

The production of sugars such as glucose from cellulosic biomass has been the focus of considerable research and development. However, the high cost and low conversion rate of many processes has limited the widespread adoption of cellulosic sugar technology.

A number of different methods for converting cellulosic biomass into sugars are known in the art. These generally include a pretreatment step wherein cellulosic biomass is physically and/or chemically altered to open up the structure of the polymeric sugars contained in cellulosic biomass and an enzymatic or chemical hydrolysis step wherein the polymeric sugars are broken down into monomeric sugars.

While high yields of glucose (>90%) based on cellulose have been reported, these yields are normally achieved at low concentrations of glucose, typically 2-5%. Methods that result in both a high yield and a high concentration of glucose are difficult to achieve because the presence of glucose typically reduces the activity of cellulase enzymes even at high enzyme loadings. Cellulase enzyme activity decreases over time, necessitating the addition of fresh enzyme to enzymatic hydrolysis reactions to maintain yield. However, the high cost of cellulase enzymes can become prohibitive. Cellulase enzymes may also bind with recalcitrant cellulose and/or lignin and become unavailable for the further hydrolysis of cellulose to glucose. This non-productive binding also hinders the recycling of enzymes, which is desirable to reduce enzyme usage and lower operating costs.

Various different processes have been developed for pretreating the cellulosic feedstock and various enzymatic hydrolysis processes have been developed to convert the treated cellulosic feedstock to sugars. For example, Parekh (PCT Publication No. WO2014/026154) describe a two-stage pre-treatment process for lignocellulosic biomass largely under acidic conditions. Schiffino et al. (US Publication No. 2011/0250645) describe methods for improving the release of monomeric sugars from alkaline treated biomass. Liu et al. (US Publication No. 2011/0300586) describe a two-stage pretreatment process for lignocellulosic biomass with the objective of reducing the crystallinity of the cellulose and to dissociate the hemicellulose-cellulose complex. Embodiments include a low severity steam treatment or autohydrolysis followed by hydrolysis with dilute acid or hot water.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figure.

According to one broad aspect, there is provided a method for activating a cellulosic feedstock in order to increase the chemical and/or enzymatic reactivity of cellulose in the feedstock. Activated cellulose may then be converted into cellulosic sugars such as by subjecting the activated cellulose to enzymatic hydrolysis.

In accordance with this aspect, the cellulosic feedstock may be subjected to a first high temperature activation step followed by a second activation step at a lower temperature under alkali conditions. In accordance with this embodiment, the method may comprise subjecting the feedstock to a first activation step wherein the feedstock is treated at a temperature greater than 190° C. and a pressure greater than 200 psig to produce a first activated cellulose stream comprising cellulose II and insoluble solids. The insoluble solids may include components of the feedstock other than cellulose such as lignin. Subsequently, the first activated cellulose stream may be subjected to a second activation step wherein the first activated cellulose stream is treated with an alkali at a lower temperature than the first activation step to produce a second activated cellulose stream comprising cellulose IV. Preferably, the first activation step is conducted in the presence of water.

Without being limited by theory, it is believed that the first activation step alters the crystalline state of cellulose in the cellulosic feedstock to produce a first activated cellulose stream with a higher proportion of cellulose II relative to the amount of cellulose II in the cellulosic feedstock. The second activation step is believed to further alter the crystalline state of cellulose in the first activated cellulose stream to produce a second activated cellulose stream with a higher proportion of cellulose IV relative to the amount of cellulose IV in the first activated cellulose stream. In one embodiment, the two-step activation method described herein produces a mixture of cellulose II, hydrated cellulose II and alkali-cellulose IV. Optionally, the cellulosic material may be treated, e.g., washed and/or filtered, after one or each activation step in order to remove soluble non-cellulosic components.

The method for activating cellulose described herein has also been determined to result in activated cellulose with an increase in the level of glucan and/or a decrease in the level of non-cellulosic components of the cellulosic feedstock such as lignin. For example, in one embodiment the methods described herein produce activated cellulose with at least 60%, at least 70% or at least 75% glucan. In one embodiment, the methods described herein produce activated cellulose with less than 25%, less than 20% or less than 15% lignin.

According to another broad aspect, methods and compositions are provided for stabilizing enzymes during enzymatic hydrolysis, maintaining enzymatic activity and/or obtaining an enzyme recycling stream.

According to another broad aspect, an enzymatic hydrolysis mix suitable for use in the enzymatic hydrolysis of cellulose is provided. In a preferred embodiment, the enzymatic hydrolysis mix is contacted with activated cellulose produced according the methods described herein.

In accordance with these aspects, there is provided one or more cellulase enzymes in combination with a surfactant and/or a dispersant for the enzymatic hydrolysis of cellulose. Without being limited by theory, it is believed that the cellulase enzymes form a complex with the surfactant and/or dispersant that may stabilize the enzymes, help maintain enzyme activity, prevent enzyme degradation and/or facilitate recovery of the enzymes following enzymatic hydrolysis. It is also believed that the presence of a dispersant such as an oligopeptide helps prevent the non-productive binding of cellulase enzymes by interacting with lignin and/or other non-cellulose components. In a preferred embodiment, the surfactant is a non-ionic surfactant such as a polysorbate surfactant. In another preferred embodiment, the surfactant is a blend of surfactants, such as Tween™, an alkoxylated glyceride and nonyl phenol. In one embodiment, the dispersant is a non-enzymatic oligopeptide, optionally a polyamino acid, optionally a polyamino acid with a molecular weight of between 500 and 10,000, between 1000 and 5000 or between 3500 and 4500. In a preferred embodiment, the polyamino acid is polyaspartic acid.

The methods and compositions described herein offer a number of advantages with respect to the activation of cellulose and/or the production of cellulosic sugars, which may be obtained from some of the embodiments. For example, in some embodiments, use of the methods and compositions described herein may result in a glucose-rich sugar stream with greater than about 12% glucose, greater than about 14% glucose, greater than about 16% glucose or greater than about 18% glucose. Further, in these or other embodiments, the methods and compositions described herein may result in a high yield of monomeric sugars. For example, in some embodiments, the methods and compositions described herein may result in a yield of glucose that is greater than about 70%, greater than about 80%, greater than about 85%, greater than about 90% or greater than about 95% of a theoretical yield of glucose. The theoretical yield of glucose in an enzymatic hydrolysis reaction may be determined based on the glucan content of the activated cellulosic material subjected to enzymatic hydrolysis. In some preferred embodiments, the methods and compositions described herein may result in a glucose rich sugar stream with both a high yield and a high concentration of glucose. For example, in one embodiment the glucose-rich sugar stream has greater than about 12% glucose and a yield of greater than 70%, or greater than 14% glucose and a yield of greater than 80%, or greater than 16% glucose and a yield greater than 90%.

According to another broad aspect, methods are provided for the enzymatic hydrolysis of activated cellulose to produce cellulosic sugars such as glucose. In accordance with this embodiment, the enzymatic hydrolysis may be conducted on as a batch process or a continuous process. The enzymatic hydrolysis may be conducted using the enzymatic hydrolysis mix and/or the activated cellulose as disclosed herein.

In accordance with another aspect, methods are provided for treating a glucose rich sugar stream to remove enzymes used for enzymatic hydrolysis. Removing and/or recycling the enzymes used for enzymatic hydrolysis may reduce the amount of enzyme needed for enzymatic hydrolysis and therefore the costs associated with producing cellulosic sugars. For example, the methods and compositions described herein may be used to recover at least 60%, at least 70%, at least 80%, or at least 85% of the cellulase enzyme activity in an enzyme recycle stream following enzymatic hydrolysis. The enzyme recycling stream may be recycled to continue treating activated cellulose and/or may be used to treat fresh activated cellulose, such as a second activated cellulose stream as described herein. In some embodiments, the glucose rich sugar stream is subjected to multiple enzyme removal treatments, either the same enzyme removal treatment repeated more than once or different enzyme removal treatments.

In accordance with another aspect, there is provided a glucose-rich sugar stream produced by a method as described herein. In one embodiment, the sugar stream comprises greater than 12%, greater than 14%, greater than 16% or greater than 18% glucose. In one embodiment, the sugar stream comprises polyaspartic acid. In some embodiments, the polyaspartic acid is present at a concentration between 1 ppb and 10000 ppm.

In accordance with another aspect, there is provided a method for producing a glucose-rich sugar stream comprising (a) providing activated cellulose comprising a mix of cellulose II, hydrated cellulose II and alkali-cellulose IV; and subjecting the activated cellulose to enzymatic hydrolysis with one or more cellulase enzymes, a surfactant and a dispersant to produce the glucose-rich sugar stream. Optionally, the activated cellulose is produced using a method a described herein.

In accordance with another aspect, there is provided a glucose-rich sugar stream further comprising a non-glucose sugar, wherein the non-glucose sugar is one or more of xylose, xylo-oligosaccharide and xylan. In one embodiment the non-glucose sugars comprise about 3-8%, about 4-7% or about 5-6% of the dry matter of the composition. In a particular embodiment the glucose-rich sugar stream comprises about 5% non-glucose sugar.

In accordance with yet a further aspect of the invention there is provided a fructose-rich sugar stream prepared by conversion of the glucose in the glucose-rich sugar stream of the invention to fructose. The fructose-rich sugar stream further comprising a non-fructose sugar, wherein the non-fructose sugar is one or more of xylose, xylo-oligosaccharide and xylan. In one embodiment the non-fructose sugars comprise about 1-8%, about 2-7% or about 3-6% of the dry matter of the composition. In a particular embodiment the fructose-rich sugar stream comprises about 5% non-glucose sugar.

In accordance with another aspect of the invention there is provided a lower glycemic index glucose syrup or lower glycemic index fructose syrup wherein the glucose or fructose syrup comprises about 1-8%, about 2-7% or about 3-6% of one or more of xylose, xylo-oligosaccharide and xylan, and wherein the glycemic index is lower than the glycemic index of conventional glucose or fructose syrup produced in a conventional manner.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description. In particular, it will be appreciated that any method may use all of the aspects disclosed herein or any particular combination or sub-combination of the aspects.

DRAWINGS

The drawings included herewith are for illustrating various examples of methods, and compositions of the teaching of the present specification and are not intended to limit the scope of what is taught in any way.

The disclosure will now be described in relation to the drawing in which.

DESCRIPTION OF VARIOUS EMBODIMENTS

Various methods and compositions will be subsequently described to provide an example of an embodiment of each claimed invention. No embodiment subsequently described limits any claimed invention and any claimed invention may cover methods and compositions that differ from those subsequently described. The claimed inventions are not limited to methods and compositions having all of the features of any one method and composition subsequently described or to features common to multiple or all of the methods and compositions described below. It is possible that a method or composition subsequently described is not an embodiment of any claimed invention. Any invention disclosed in an method or composition subsequently described that is not claimed in this document may be the subject matter of another protective instrument, for example, a continuing patent application, and the applicants, inventors or owners do not intend to abandon, disclaim or dedicate to the public any such invention by its disclosure in this document.

Described herein are various methods and compositions useful for the treatment of cellulosic biomass to produce cellulosic sugars. In one embodiment, there is provided a method for activating a cellulosic feedstock to produce activated cellulose. It has been determined that subjecting a cellulosic feedstock to a first activation step at a high temperature and pressure followed by a second activation step with an alkali at a lower temperature than the first activation step produces activated cellulose with chemical and/or physical properties that are advantageous for the hydrolysis of cellulose into monomeric sugars.

Figure 1:
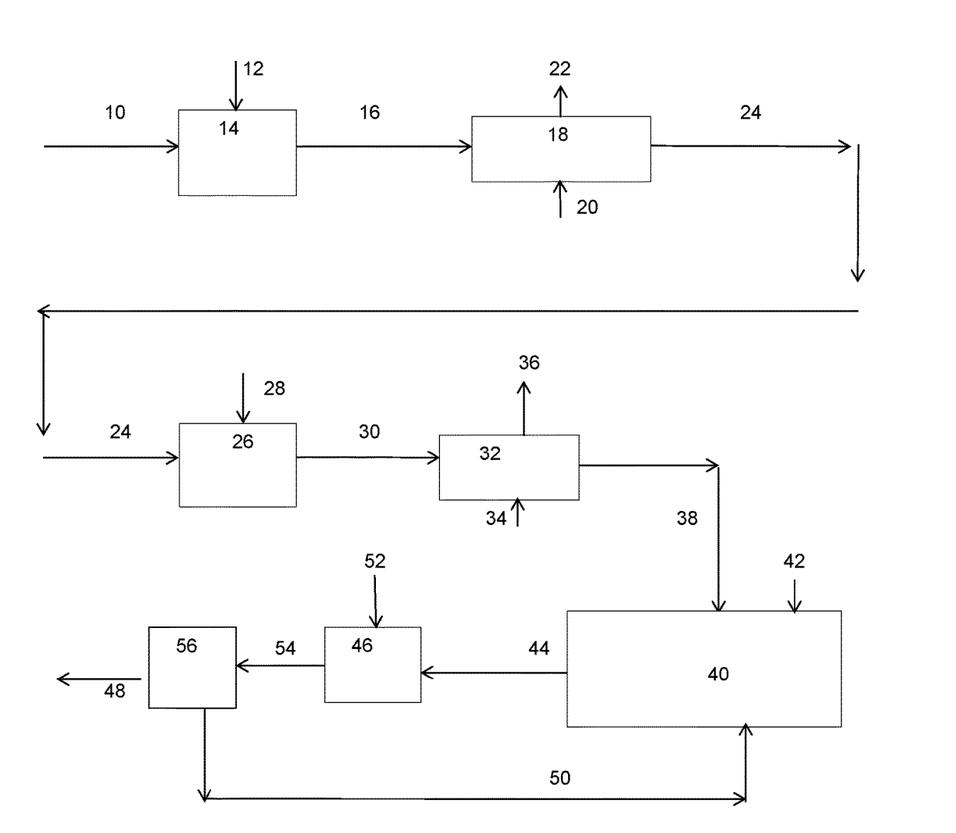
FIG. 1 is a schematic flow chart of the method according to a preferred embodiment that includes a two-step activation of a cellulosic feedstock, enzymatic hydrolysis of the activated feedstock and an enzyme removal treatment to obtain an enzyme recycle stream and a glucose-rich and enzyme-poor sugar stream.

The methods disclosed herein utilize a cellulosic feedstock 10. Cellulosic feedstock 10 may be any feedstock known in the cellulosic sugar art. For example, the cellulosic feedstock may comprise one or more of straw, corn stover, bagasse, hardwoods, softwoods, energy crops and the like.

The raw agricultural material which is provided to a plant may be treated to remove rocks, soil and other material present in the raw agricultural material and to reduce the size of the raw agricultural or forest based material that is fed to the process, such as by comminution, grinding, milling or otherwise treated.

As exemplified in FIG. 1, cellulosic feedstock 10 may be fed to reactor 14 wherein cellulosic feedstock 10 is subjected to a first activation step to produce a first activated cellulose stream 16. In the first activation step, cellulosic feedstock 10 may be treated at an elevated temperature and pressure to produce first activated cellulose stream 16 comprising cellulose II and insoluble solids.

Reactor 14 may be a batch reactor or a continuous process reactor. In the case of a batch reactor, cellulosic feedstock 10 may be fed to reactor 14 and the reactor, which may be a stirred tank reactor, may be raised to the operating conditions for a desired time. If reactor 14 is a continuous flow reactor, then it may be a steam exposition reactor as is known in the art and may be maintained at the desired operating condition.

The first activation step may be conducted under conditions that increase the amount of cellulose II in the first activated cellulose stream relative to the amount of cellulose II in the feedstock.

The temperature may be greater than 190° C. and optionally greater than 210° C., preferably greater than 220° C. and may be less than about 250° C. Accordingly, the process may be conducted at a temperature in the range of 190° C.-250° C., 210° C.-250° C., 220° C.-240° C., or 222° C.-230° C.

The pressure may be greater than 200 psig and optionally less than 500 psig. Pressure in the reactor corresponds to temperature as per saturated steam thermodynamics as a minimum. In an embodiment, pressure may be increased over and above that value by adding a pressurized gas, or adding superheat.

Cellulosic feedstock 10 may be subjected to the first activation step for less than 30 minutes, less than 20 minutes, less than 10 minutes or less than 5 minutes. The duration of the treatment time will vary depending upon many factors including severity of the activation step, e.g., the temperature and pressure of reactor 14.

It will be appreciated that the temperatures, pressures and duration of treatment may be combined in any desired combination. Accordingly, for example, the first activation step may comprise subjecting the feedstock to a pressure between 200 and 500 psig and a temperature between 200 and 250° C. for 1 to 30 minutes, or a pressure between 200 and 500 psig and a temperature between 190 and 215° C. for less than 4 minutes.

Optionally, the first activation step is conducted in the presence of water. Water may be introduced into reactor 14 by one or more of being present in cellulosic feedstock 10, being present in reactor 14 when cellulosic feedstock is introduced into reactor 14 and by being introduced by feed stream 12. The total amount of moisture that is introduced into the reactor may be at least 30% and can be as high as 90%. In a particular embodiment, there is 50% moisture going into the reactor.

The water which is present in reactor 14 may be in the form of steam or liquid water and is preferably in the form of liquid water. It will be appreciated that the temperature and pressure of the first activation step may be selected such that liquid water is present in the reactor 14.

First activated cellulose stream 16 may have a solids content of between about 30% and 50% solids by weight. The solids will comprise chiefly cellulose which may be subsequently subjected to a second activation step. The solids may further comprise lignin, hemicellulose and minor components such as ash, protein, or extractives.

Optionally, the cellulosic material may be subjected to one or more washing steps, either under the same conditions or different conditions, after the first and/or second activation step. To this end, first activated cellulose stream 16 may be subjected to one or more washing steps prior to the second activation step in order to remove soluble non-cellulosic components such as hemicellulose and some ash, extractives and lignin. The first wash removes these solubles and, because the solubles are at acidic pH, the wash step also reduces the alkali requirement in the second alkali activation stage.

As exemplified in FIG. 1, first activated cellulose stream 16 and wash water 20 may be introduced to wash reactor 18 to produce waste water 22 and a washed first activated cellulose stream 24.

Wash water 20 may be hot water, such as water at a temperature between about 40° C. and 100° C. or between about 50° C. and 95° C. Waste water stream 22 may be treated and recycled in the process or elsewhere or discarded.

Wash reactor 18 may be any design known in the art. Optionally, wash reactor 18 may be operated counter-currently and it may be a counter-current belt filter. Other filtration or separation methods may be used such as a filter press, twin wire press, twin roll press, rotary vaccum filter or a centrifuge.

As exemplified in FIG. 1, washed first activated cellulose stream 24 may be fed to reactor 26 wherein washed first activated cellulose stream 24 is subjected to a second activation step to produce a second activated cellulose stream 30. In alternate embodiments, some or all of first activated cellulose stream may be introduced into reactor 26. The following description is based on FIG. 1 which exemplifies the use of a first wash step. In the second activation step, washed first activated cellulose stream 24 may be treated with an alkali at a lower temperature than the first activation step to produce a second activated cellulose stream comprising cellulose IV.

Reactor 26 may be batch reactor or a continuous process reactor. In the case of a batch reactor, washed first activated cellulose stream 24 may be fed to reactor 26 and the reactor, which may be a stirred tank reactor, may be raised to the operating conditions for a desired time. If reactor 26 is a continuous flow reactor, then it may be a steam exposition reactor as is known in the art and may be maintained at the desired operating condition.

The second activation step may be conducted under conditions that increase the amount of cellulose IV in the second activated cellulose stream relative to the amount of cellulose IV in the washed first activated cellulose stream 24.

The temperature is optionally greater than 60° C., and may be less than about 180° C., less than about 160° C., less than 140° C., less than about 120° C., less than about 100° C. or less than about 80° C. Accordingly the process may be conducted at a temperature in the range of 60° C.-180° C., 60° C.-160° C., 60° C.-140° C., 60° C.-120° C., 60° C.-100° C. or 60° C.-80° C.

Optionally, the second activation step is conducted at superatmospheric pressure. For example, the superatmospheric pressure may be a pressure between about 0.1 and 400 psig.

Washed first activated cellulose stream 24 may be subjected to the second activation step for less than less than 180 minutes, less than 120 minutes, less than 90 minutes or less than 60 minutes and optionally more than 15 minutes, more than 30 minutes, or more than 45 minutes. The duration of the treatment time will vary depending upon many factors including severity of the activation step, e.g., the temperature and pressure of reactor 26.

It will be appreciated that the temperatures, pressures and duration of treatment may be combined in any desired combination. Accordingly, for example, the second activation step may comprise subjecting the first activated cellulose stream to a temperature between 60 and 240° C. for 15 to 120 minutes at a pressure of 0 to 500 psig or a temperature between 80 and 150° C. for at least 60 minutes at a pressure of 0 to 300 psig.

As exemplified in FIG. 1, the second activation step preferably comprises treating the first activated cellulose stream in the presence of an alkali. The alkali may be introduced into reactor 26 in any manner. For example, as exemplified, alkali stream 28 is introduced separately into reactor 26. It will be appreciated that alkali stream 28 may be introduced into reactor 26 prior to, concurrently with or subsequent to the introduction of washed first activated cellulose stream 24 into reactor 26. Alternately alkali stream 28 may be introduced into washed first activated cellulose stream 24 and a combined stream then introduced into reactor 26.

The alkali may comprise one or more of sodium hydroxide, potassium hydroxide, magnesium hydroxide and ammonia. In one embodiment, the alkali is sodium hydroxide. In one embodiment, the alkali is loaded at between about 10% and 1%, between about 7% and 2% or preferably less than 6% of the total insoluble solids in first activated cellulose stream 24. The alkali swells cellulose and further breaks inter and intramolecular hydrogen bonds of the cellulose, thereby further modifying crystalline structure.

Optionally, the second activating step may be performed in the presence of an oxidizing agent and/or an enzyme such as a laccase and/or a lignin modifying enzyme.

Examples of oxidizing agents suitable for use in the second activation step include, but are not limited to hydrogen peroxide ($H_2O_2$). In one embodiment, the oxidizing agent is loaded at less than about 2% and/or greater than about 0.0001% of the total insoluble solids in the first activated cellulose stream 16/24. In one embodiment, the oxidizing agent is loaded at less than about 1%, less than about 0.1% or less than about 0.001% of the total insoluble solids in the first activated cellulose stream 16/24, optionally between about 1% and 0.0001%.

Examples of enzymes suitable for use in the second activation step include, but are not limited to lignin modifying enzymes such as laccase oxidizing enzyme.

Second activated cellulose stream 30 may have a solids content of between about 5% and 50% solids by weight, preferably between about 20% and 35% solids. The solids will comprise chiefly cellulose which may optionally be recovered and recycled. Other components will be hemicellulose and lignin, both less than 20%.

Optionally, second activated cellulose stream 30 may be subjected to one or more washing steps after activation to remove alkali and solubilized lignin.

Second activated cellulose stream 30 and wash water 34 may be introduced to wash reactor 32 to produce waste water 36 and a washed second activated cellulose stream 38. Wash reactor 32 may be operated in a similar manner to wash reactor 18 or differently.

Wash water 34 may be hot water, such as water at a temperature between about 50° C. and 95° C. or between about 60° C. and 95° C. Waste water stream 36 may be treated and recycled in the process or elsewhere or discarded.

Wash reactor 32 may be any design known in the art. Optionally, wash reactor 32 may be operated counter-currently and it may be a counter-current belt filter. Other filtration or separation methods may be used, such as filter press, twin wire press, twin roll press, rotary vacuum filter or centrifuge.

An advantage of subjecting a cellulosic feedstock to a first activation step at a high temperature followed by a second activation step at a lower temperature under alkali conditions has been shown to increase the level of glycan and decrease the level of lignin in second activated cellulose stream 30 relative to a feedstock only subjected to a first high temperature activation step. Without being limited by theory, it is believed that the two-step activation process described herein alters the crystallinity of cellulose in the feedstock and improves the physical and/or chemical characteristics of the cellulose for enzymatic hydrolysis. In one embodiment, the two-step activation process results in activated cellulose comprising cellulose II and alkali-cellulose IV.

A skilled person will appreciate that cellulose exists in several different crystalline structures, corresponding to the location of hydrogen bonds between and within strands. For example, naturally occurring cellulose found in cellulosic biomass is cellulose I, with structures $I_\alpha$ and $I_\beta$. Cellulose in regenerated cellulose fibers is typically cellulose II. Regenerated cellulose fibers refers to fibers produced by the viscose process for viscose production of cellophane or rayon. The conversion of cellulose I to cellulose II is irreversible. The structures of cellulose III and cellulose IV may be produced through various chemical treatments. The different crystalline forms of cellulose can be identified by characteristic X-ray diffraction patterns. Cellulose and the different crystalline structures of cellulose are further described in Perez and Samain, "Structure and Engineering of Cellulose" *Advances in Carbohydrate Chemistry and Biochemistry*, Vol. 64, Elsevier (2010), which is hereby incorporated by reference in its entirety.

Washed second activated cellulose stream 38 may be subjected to enzymatic hydrolysis in enzymatic hydrolysis reactor 40 with one or more cellulase enzymes 42 to produce a glucose-rich sugar stream 44. It will be appreciated that some or all of second activated cellulose stream 30 may be subjected to enzymatic hydrolysis and accordingly only a part or none of second activated cellulose stream 30 may be subjected to washing. The following description may apply to second activated cellulose stream 30 whether or not subjected to a washing step.

It has surprisingly been determined that the activated cellulose containing cellulose II (which may be a combination of cellulose II and hydrated cellulose II) and cellulose IV (which may be alkali-cellulose IV) which may be produced by the two step activation process disclosed herein is particularly susceptible to enzymatic hydrolysis. In particular, the activated cellulose has shown a surprising ability to adsorb cellulase enzymes. Contacting the activated cellulose with one or more cellulase enzymes in a glucose rich sugar stream may initially result in the enzymes being adsorbed to the activated cellulose. The cellulose may then be removed from the glucose-rich sugar stream and optionally introduced into enzymatic hydrolysis reactor 40.

Therefore, the activated cellulose produced by any method disclosed herein may be subject to enzymatic hydrolysis to break the cellulose down into cellulosic sugars such as glucose. Alternately the enzymatic hydrolysis process disclosed herein may be used with any conventional enzymatic hydrolysis cellulosic feedstock.

Accordingly, activated cellulose, optionally a second activated cellulose stream as described herein may be contacted with one or more cellulase enzymes to produce the glucose-rich sugar stream. As exemplified in FIG. 1, washed second activated cellulose stream 30 and enzyme stream 42 are introduced into enzymatic hydrolysis reactor 40 to produce glucose rich sugar stream 44. Washed second activated cellulose stream 30 may be introduced into enzymatic hydrolysis reactor 40 prior to, concurrently with or subsequent to the introduction of enzyme stream 42 into reactor 40. Alternately, or in addition, enzyme stream 42 may be introduced into washed second activated cellulose stream 30 and the combined stream may be introduced into enzymatic hydrolysis reactor 40.

Enzymatic hydrolysis reactor 40 may be any enzymatic hydrolysis reactor known in the art and may operate on a batch or continuous basis. Enzymatic hydrolysis reactor 40 may operate at any conventional temperatures and pressures, cellulose loading, enzyme loading and the like. For example, enzymatic hydrolysis reactor 40 may operate at a temperature range of 40° C. to 55° C.

The cellulase enzymes may be selected to break cellulose down into monomeric sugars. For example, the cellulase enzymes may be selected to hydrolyze 1,4-beta-D-glycosidic linkages into monosaccharides. The one or more cellulase enzymes may comprise an enzyme with at least one of cellobiohydrolase, endoglucanase and beta-glucosidase activity. While cellulase enzyme preparations may be isolated from a number of sources such as natural cultures of bacteria, yeast or fungi a person skilled in the art will appreciate using enzymes produced using recombinant techniques. Examples of commercially available enzymes suitable for use with the methods described herein include, but are not limited to, Novozymes Ctec 2 or 3, AB Enzymes Rohament.

The one or more cellulase enzymes may be added at a loading of 0.1 to 120 mg, 0.2 to 60 mg or 1 to 30 mg of enzyme protein per gram of glucan. In one embodiment, the cellulase enzymes are added at a loading of 0.1 to 5 mg of enzyme protein per gram of glucan in the activated cellulose. In one embodiment, the one or more cellulase enzymes are added to the activated cellulose at a loading of about 2 to about 60 Filter Paper Units (FPU)/g of glucan, or optionally at a loading of about 2 to 30 or 1 to 15 FPU/g of glucan. The one or more cellulase enzymes may be added separately to the activated cellulose directly or first combined with a surfactant and/or dispersant as described subsequently.

The one or more cellulase enzymes may be contacted with the activated cellulose for a suitable length of time (e.g., for between 24-144 hours, between 48-144 hours, between 48-60 hours or between 24 and 72 hours) to in order to convert the cellulose into monomeric sugars through enzymatic hydrolysis.

In some embodiments, at least about 70%, 75%, 80%, 85%, 90%, or 95% of the theoretical yield of glucose based on the glycan content of the activated cellulose is converted to glucose during enzymatic hydrolysis to produce a glucose-rich sugar stream. In some embodiments, enzymatic hydrolysis is conducted for a predetermined length of time or until a predetermined yield of glucose is obtained. After a certain amount of time, the rate of glucose production from the enzymatic hydrolysis of cellulose may decrease as the cellulose substrate is depleted or the presence of glucose inhibits the activity of the cellulase enzymes.

Optionally, an activated cellulose may be contacted with one or more cellulase enzymes in the presence of a surfactant and/or a dispersant. In a preferred embodiment, the dispersant is polyaspartic acid.

It has surprisingly been determined that subjecting activated cellulose, particularly the activated cellulose disclosed herein, to enzymatic hydrolysis in the presence of a surfactant and/or a dispersant such as polyaspartic acid offers a number of advantages for the production of monomeric sugars. For example, the presence of the surfactant and/or dispersant may increase cellulase enzyme stability, help protect the cellulase enzymes from degradation, prevent irreversible binding and/or improve cellulase enzyme activity. The presence of the surfactant and/or dispersant is also believed to improve the recovery of cellulase enzymes into an enzyme recycle stream following enzymatic hydrolysis. For example, in some embodiments cellulase enzymes may be used for the enzymatic hydrolysis of activated cellulose, removed from the resulting glucose-rich sugar stream and recycled to enzymatic hydrolysis reactor 40 or contacted with fresh activated cellulose for further enzymatic hydrolysis. In some embodiments, cellulase enzymes may be used and recycled in at least 3 or 4 rounds of enzymatic hydrolysis, each cycle lasting between 48 and 72 hours.

The surfactant may be a non-ionic surfactant, optionally a polysorbate surfactant such as Tween. The surfactant may also be a blend of surfactants. In a preferred embodiment the surfactant is a blend of Tween 80, an alkoxylated glyceride and nonyl phenol. In one embodiment, the surfactant is present at a loading of less than about 2% and/or greater than about 0.01%. In one embodiment, the surfactant is present at a loading between 1% and 0.01%, between 0.5% and 0.05% or between about 0.1% and 0.2% of the weight of the cellulose content in the activated cellulose.

The dispersant may be an oligopeptide, optionally a non-enzymatic polypeptide with molecular weight between 500 and 10,000 or between 1000 and 5000. The oligopeptide may be polyaspartic acid. The polyaspartic acid may have a molecular weight between 500 and 10,000, between 1000 and 5000 or between 3500 and 4500. The polyaspartic acid may be present at a loading of less than about 2% and/or greater than about 0.001% of the weight of the cellulose content in the activated cellulose. In some embodiments, the polyaspartic acid is present at a loading between 1% and 0.001%, between 0.25% and 0.025%, or about 0.1% of the weight of the cellulose content in the activated cellulose.

Optionally, the ratio of surfactant to dispersant (e.g., polyaspartic acid) in the enzymatic hydrolysis mix is from 0.1:1 to 10:1, optionally from 0.5:1 to 2:1.

Optionally, the molar ratio of dispersant (e.g., polyaspartic acid) to the one or more cellulase enzymes is from 0.01 to 10:1.

Accordingly, an enzymatic hydrolysis mix comprising one or more cellulase enzymes, one or more surfactants and one or more dispersants may be used in any enzymatic hydrolysis process or may be used in association with any of the activation and enzymatic hydrolysis processes disclosed herein. The enzymatic hydrolysis mix is particularly suitable for the enzymatic hydrolysis of activated cellulose comprising cellulose II and cellulose IV as described herein.

The one or more cellulase enzymes, the surfactant and the dispersant may be introduced singularly or in combinations or sub-combinations into enzymatic hydrolysis reactor 40. For example, they may each be combined separately with the activated cellulose (e.g., each may be sequentially added to stream 38 or stream 38 may be divided into 3 streams and the cellulase enzymes, the surfactant and the dispersant may each be added to one of the divided out streams) prior to introducing stream 38 into reactor 40. Alternatively, the one or more cellulase enzymes, the surfactant and the dispersant may be combined together to form stream 42 prior to combining the mixture with the activated cellulose (e.g., introducing stream 42 into reactor 40 or introducing stream 42 into stream 38 prior to introducing stream 38 into reactor 40). Combining the enzymes, surfactant and the dispersant together prior to contacting the activated cellulose is believed to facilitate the formation of a ternary complex that helps stabilize the enzyme and prevent enzyme degradation. Accordingly, the one or more cellulase enzymes may be combined with the surfactant and the dispersant prior to subjecting the activated cellulose to enzymatic hydrolysis. For example, the one or more cellulase enzymes may be combined with the surfactant and the dispersant for at least 5 seconds, at least 10 seconds, at least 30 seconds or at least 1 minute prior to contacting them with the activated cellulose (e.g., stream 38) or prior to subjecting the activated cellulose to enzymatic hydrolysis.

As exemplified in FIG. 1, glucose-rich sugar stream 44 may be subjected to an enzyme removal step to obtain a glucose-rich and enzyme-poor sugar stream 48 and an enzyme recycle stream 50. The enzyme removal step may be any enzyme removal step known in the art and may be conducted in any equipment known in the art. Optionally, the enzyme removal step comprises contacting glucose-rich sugar stream 44, e.g., for a limited time, with cellulose, which may be an activated cellulose produced by any method disclosed herein.

For example, the enzyme removal step may comprise:
(a) contacting the glucose-rich sugar stream including enzymes with cellulose and obtaining cellulose with enzymes adsorbed thereon; and,
(b) subjecting the glucose-rich sugar stream to a cellulose removal step to obtain the glucose-rich and enzyme poor sugar stream which has a reduced level of cellulose and the enzyme recycle stream.

Optionally, step (a) comprises contacting the glucose-rich sugar stream with activated cellulose, optionally a second activated cellulose stream produced according to methods described herein.

Without being limited by theory, it is believed that enzymes in the glucose-rich sugar stream adsorb onto the cellulose such that removing the cellulose from the glucose-rich sugar stream removes enzymes from the stream and results in glucose-rich and enzyme-poor sugar stream 48 and enzyme recycle stream 50. In a particularly preferred embodiment, the cellulase enzymes in the glucose-rich sugar stream are in the presence of a surfactant and a dispersant and the enzymes in glucose-rich sugar stream 44 are removed by contacting glucose rich sugar stream 44 with activated cellulose 16, 24, 30, 38 produced using the methods described herein.

Accordingly a cellulose stream 52 may be introduced into reactor 46. Reactor 46 may comprise any reactor which may enable glucose-rich sugar stream 44 and cellulose to contact each other so as to withdraw enzymes from the solution and to separate the cellulose with the enzymes absorbed thereon. Accordingly, for example, reactor 46 may comprise a stirred tank reactor or a plug flow reactor for mixing the glucose-rich sugar stream and cellulose to produce a mixed stream 54.

The glucose-rich sugar stream and cellulose may be contacted together for less than about 2 hours, less than about 90 minutes or less than about 60 minutes and may be contacted together for between about 10 minutes and 60 minutes, or between about 30 minutes and 90 minutes.

Subsequently, mixed stream 54 is subjected to a solid liquid separation step is a separator 56. Separator 56 may be any separator known in the arts. Separator 56 may use any separation technique known in the art such a filtration, decantation, gravity separation, centrifugation, or use of a press. For Example, separator 56 may comprise a filter, press, optionally a twin screw press, a twin wire press or a twin roll press.

Enzyme recycle stream 50 may be a high solids stream. For example, enzyme recycle stream may comprise greater than about 30%, greater than about 40% or greater than about 50% cellulosic solids.

Enzyme recycle stream 50 may be used for conducting enzymatic hydrolysis on fresh activated cellulose. Alternately, enzyme recycle stream 50 may be recycled to reactor 40. Accordingly, if reactor 40 is operated on a batch basis, a purge stream of glucose-rich sugar stream may be withdrawn and treated to obtain recycle stream 50. Surprisingly, it has been determined that enzymes recycled by this process generally maintain their activity after being recycled once, twice, three times or even four times. As a result, glucose-rich sugar stream 48 may comprise greater than about 12% glucose, greater than about 14% glucose, greater than about 16% glucose or greater than about 18% glucose. Further, a yield of glucose that is greater than about 70%, greater than about 80%, greater than about 85%, greater than about 90% or greater than about 95% of a theoretical yield of glucose may be obtained.

Optionally, glucose-rich sugar stream 48 may comprises a detectable level of polyaspartic acid. In one embodiment, the sugar stream comprises between about 1 ppb and 10000 ppm polyaspartic acid.

It has surprisingly been found that the glucose-rich sugar stream resulting from the enzymatic hydrolysis of the activated cellulose disclosed herein contains about 5% non-glucose sugars which are one or more of xylose, oligomers of xylose (xylo-oligosaccharide) and xylan. Xylo-oligosaccharides as described herein refer to polymers of xylos having a degree of polymerization (dp) of about 2 to about 10. Xylan as described herein refers to polymers of xylose having a degree of polymerization (dp) of >10.

In a particular aspect the enzymatic hydrolysis of the activated cellulose may be carried out using the hydrolysis mix as disclosed herein. In a further aspect the glucose rich sugar stream is prepared using the cellulose activation method and/or the enzyme hydrolysis method described herein.

Glucose obtained from sources such as corn using standard methods are also known to have about 5% non-glucose sugars. However, the non-glucose sugars found in corn glucose are higher glycemic index sugars such as maltose, maltotriose, higher saccharides of dextrose.

In one embodiment the non-glucose sugars found in the glucose rich sugar stream disclosed herein comprise about 1-8%, about 2-7% or about 3-6% of the dry matter of the composition and are one or more of xylose, xylo-oligosaccharides and xylan. In a particular embodiment the dry matter of the glucose-rich sugar stream was found to comprise 95% glucose, 4% xylose, 1% xylo-oligosaccharides.

Glucose obtained from the methods disclosed herein can be converted to fructose using known methods such as glucose isomerization to fructose as described, for example, by S. Z. Dziedzic et al., "Handbook of starch hydrolysis products and their derivatives" Dec. 31, 1995, pages 55-58, which is hereby incorporated herein by reference. It has been found that the fructose obtain from conversion of the glucose of obtained from the methods disclosed herein also contains about 3-5% non-glucose sugar wherein the non-glucose sugar is xylose and/or oligomers of xylose.

In accordance with a further aspect of the invention there is provided a fructose-rich sugar stream prepared by conversion of the glucose in the glucose-rich sugar stream disclosed herein to fructose. The fructose-rich sugar stream also comprises non-fructose sugar, wherein the non-fructose sugar is one or more of xylose, xylo-oligosaccharide and xylan. In one embodiment the non-fructose sugars comprise about 1-8%, about 2-7% or about 3-6% of the dry matter of the composition.

In accordance with another aspect of the invention there is provided a lower glycemic index glucose product or lower glycemic index fructose product wherein the glucose product or fructose product comprises about 1-8%, about 2-7% or about 3-6% preferably 5% non-glucose or non-fructose sugar and wherein the non-glucose or non-fructose sugar is one or more of xylose, xylo-oligosaccharides and xylan.

In a further aspect the glycemic index of the glucose product or fructose product is lower than the glycemic index of conventional glucose or fructose syrup produced in a conventional manner. The glycemic index (GI) can be measured using methods known in the art for example as described in "In vitro method for predicting glycemic index of foods using simulated digestion and an artificial neural network" R. L. Magaletta et al., Cereal Chemistry vol. 87, no. 4, 2010.

The glucose product or fructose product obtained by the methods described herein can be substituted for higher glycemic index glucose or fructose in production of various foods and drinks to provide a lower glycemic index product. Lower glycemic index foods and drinks may provide health advantages in the management of blood sugar and insulin levels which may in turn reduce the risk of heart disease and/or diabetes. Foods having a lower glycemic index may also be useful in controlling appetite and weight loss.

It will be appreciated that one or more of the embodiments described herein for the activation of a cellulosic feedstock may be used together with one or more embodiments described herein for the enzymatic hydrolysis of cellulose in order to produce cellulosic sugars from a cellulosic feedstock.

What has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

While the above disclosure generally describes the present application, a more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Treatment of Sugarcane Bagasse for Activating Cellulose

Various methods for activating cellulose were investigated using sugarcane bagasse. Sugarcane bagasse was subjected to either a first steam treatment step 220° C., 5 minutes residence time followed by a hot water wash using water at 80° C. or a first steam treatment followed by treatment with alkaline hydrogen peroxide. Alkali wash at 90° C., 60 minutes or 120 minutes, and 1% peroxide loading on solids.

As shown in Table 1, the use of the two-step treatment with a steam treatment step followed by alkaline hydrogen peroxide significantly increased the level of glucan and decreased the amount of lignin relative to treatment with steam and a hot water wash.

TABLE 1

Influence of alkaline peroxide treatment on the chemical composition of the water insoluble component of steam pretreated and subsequently hot water washed sugarcane bagasse* (% dry weight). AHP-60 and AHP-120 refer to 60 minute and 120 minute treatments.

|  | Steam pretreated and hot water washed | AHP - 60* | AHP - 120** |
|---|---|---|---|
| Arabinan | BDL**** | BDL | BDL |
| Galactan | BDL | BDL | BDL |
| Glucan | 48.3 (0.7) | 79.3 (1.4) | 78.2 (0.7) |
| Xylan | 3.6 (0.1) | 3.7 (0.1) | 3.7 (0.1) |
| Mannan | BDL | BDL | BDL |
| Lignin (Acid insoluble)** | 41.6 (1.6) | 12.9 (0.3) | 12.9 (0.3) |
| Acid soluble lignin | 0.7 (0.0) | 0.6 (0.0) | 0.5 (0.0) |
| Ash | 3.2 (0.4) | 1.7 (0.4) | 1.9 (0.7) |

*Alkaline hydrogen peroxide treatment
**Alkaline hydrogen peroxide treatment
***A minor fraction of the lignin may contain ash components
****Below detectable level Example 2

Enzymatic Hydrolysis of Activated Sugarcane Bagasse

The water insoluble cellulosic components prepared in Example 1 were then subjected to enzymatic hydrolysis for 72 hours. Comet additive S-001, comprising a mixture of a surfactant Tween 80 and a dispersant polyaspartic acid with a MW of 3500-4500 in a 1:1 ratio was also added to the enzymatic hydrolysis mix for the alkali treated sugar cane bagasse.

As shown in Table 2, enzymatic hydrolysis of alkali treated sugar bagasse in the presence of the Comet additive S-001 resulted in a glucose yield of 105.1 grams of glucose per gram of glucan, approaching the theoretical yield of ~110 grams of glucose per gram of glucan.

TABLE 2

Monomeric glucose yield after the 72 hour enzymatic hydrolysis of the water insoluble cellulosic component of steam pretreated and subsequently alkaline peroxide treated sugarcane bagasse (expressed as g per 100 g glucan**).

| Substrate | Glucose yield |
|---|---|
| Hot water washed sugar cane bagasse | 79.1 (2.6)*** |
| Alkali treated sugar cane bagasse + Comet additive-S-001 | 105.1 (1.5) |

* Cellulase loading: 31 mg protein per g of glucan
**100 g glucan should theoretically release ~110 g glucose.
***Values in the bracket represent standard deviations of triplicates Furthermore, as shown in Table 3, enzymatic hydrolysis in the presence of Comet additive S-001 did not alter the yield of monomeric xylose compared to alkali treated sugarcane bagasse subject to enzymatic hydrolysis without the additive. Accordingly, the additive did not adversely affect the yield.

TABLE 3

Monomeric xylose yield after the 72 hour enzymatic hydrolysis* of the water insoluble cellulosic component of steam pretreated and subsequently alkaline peroxide treated sugarcane bagasse (expressed as g per 100 g substrate**).

| Substrate | Xylose yield |
|---|---|
| Alkali treated sugarcane bagasse | 2.7 (0.2)*** |
| Alkali treated sugarcane bagasse + Comet additive-S-001 | 2.7 (0.1) |

*Refer to Table 2 for enzymatic hydrolysis conditions
**100 g substrate should theoretically release 4.1 g xylose (refer to Table 1 for xylan content).
***Values in the bracket represent standard deviations of triplicates Analysis of the fraction of the total protein content present in the supernatant after 72 hours of enzymatic hydrolysis is shown in Table 4. The use of Comet additive S-001 resulted in a higher fraction of total protein, indicative of the higher levels of enzymes within the supernatant and improved enzyme stability.

TABLE 4

Fraction of the total protein present in the supernatant after 72 hours (expressed as g per 100 g protein added**).

| | Fraction of the total proteins in the liquid |
|---|---|
| Hot water washed sugar cane bagasse | — |
| Alkali treated sugarcane bagasse | 61.2 (2.2) |
| Alkali treated sugarcane bagasse + Comet additive-S001 | 77.2 (1.1)** |

**Values in the bracket represent standard deviations of triplicates

The alkali treated sugarcane bagasse was subject to multiple rounds of recycle hydrolysis in the presence of Comet additive S-001. As shown in Table 5, recycle hydrolysis was able to produce a high yield and a high concentration of glucose with minimal loss of enzymes over repeated rounds of enzymatic hydrolysis.

TABLE 5

Results of the recycle hydrolysis (Total 16% glucan)* of the water insoluble cellulosic component of steam pretreated and subsequently alkaline peroxide treated sugarcane bagasse.

| Hydrolysis interval and substrate addition | Glucose yield (%) | Glucose concentration (% wt/vol.) | Xylose yield*** | Dissolved solids (wt/wt) | Fraction of the proteins in the supernatant***** |
|---|---|---|---|---|---|
| After 48 hours** | 83.9 (1.4)**** | 16.1 (0.3) | 1.9 (0.2) | 19.1 (0.2) | 58.4 (1.3) |
| After next 48 hours | 83.1 (0.9) | 15.9 (0.2) | 2.2 (0.0) | 18.8 (0.2) | 60.1 (2.4) |
| After next 48 hours | 90.9 (0.3) | 18.2 (0.1) | 2.5 (0.0) | 20.9 (0.1) | 64.2 (0.8) |
| After next 48 hours | 92.3 (2.1) | 18.1 (0.4) | 2.3 (0.1) | 20.7 (0.5) | 67.7 (1.5) |

*16% glucan loading (~20% solids loading) of the alkali treated substrate. The reaction was conducted at a total 20 L scale.
**Cellulase loading: 31 mg protein per g of glucan added in the beginning of the hydrolysis. 0.2% S-001 in the reaction mixture, 6 mg supplement enzyme protein per recycle
***expressed as g/100 g substrate. 100 g substrate should theoretically release 4.1 g xylose (refer to Table 1 for xylan content).
****Values in the bracket represent standard deviations of triplicates
*****Does not account for enzyme adsorbed onto substrate

Example 3

Treatment of Wheat Straw for Activating Cellulose

Methods for activating a cellulose feedstock were investigated using wheat straw. Wheat straw was subjected to a first steam treatment step at 220° C., 5 minute residence time, followed by a hot water wash at 80° C., followed by alkaline wash at 90° C. for 60 minutes and 1% peroxide loading on solids.

As shown in Table 6, the use of the two-step treatment with alkaline hydrogen peroxide resulted in water insoluble components with a high level of glucan (75.1%).

TABLE 6

Chemical composition of the water insoluble component of steam pretreated and subsequently alkaline peroxide treated wheat straw* (% Dry weight)

| | |
|---|---|
| Arabinan | BDL*** |
| Galactan | BDL |
| Glucan | 75.1 (0.6) |
| Xylan | 8.1 (0.1) |
| Mannan | BDL |
| Lignin (Acid insoluble)** | 13.5 (0.4) |
| Acid soluble lignin | 0.4 (0.0) |
| Ash | 1.2 (0.3) |

*Solids yield after the peroxide treatment was 75.7. Alkaline peroxide treatment was conducted at 10% consistency, pH 11.5 and 1% peroxide solution, 80° C. for 2 hours.
**A minor fraction of the lignin may contain ash components
***Below detectable level

Example 4

Enzymatic Hydrolysis of Activated Wheat Straw

The water insoluble cellulosic components of steam treated wheat straw or steam treated and subsequently alkali treated wheat straw were subject to enzymatic hydrolysis as shown in Tables 7-9. The surfactant Tween 80 was also added, as noted in the table.

TABLE 7

Monomeric glucose yield during the enzymatic hydrolysis (10% glucan loading)* of the water insoluble cellulosic component of steam pretreated and subsequently alkaline peroxide treated wheat straw (expressed as g per 100 g glucan**).

| | 24 hours | 72 hours |
|---|---|---|
| Hot water washed wheat straw | —**** | 85.0 (2.1) |
| Hot water washed wheat straw + Tween 80*** | — | 89.1 (0.5) |
| Peroxide treated wheat straw | 83.7 (1.1)***** | 97.0 (0.3) |
| Peroxide treated wheat straw + Tween 80 | 90.4 (0.1) | 102.3 (2.9) |

*13.3% solids loading for peroxide treated substrate & 17.9% solids loading for steam pretreated wheat straw in order to obtain 10% glucan loading. Cellulase loading: 31 mg protein (CTec 2) per g of glucan
**100 g glucan should theoretically release ~110 g glucose.
***0.2% Tween 80 in the reaction mixture
****was not liquefied enough to obtain a representative sample for analysis
*****Values in the bracket represent standard deviations

TABLE 8

Monomeric xylose yield after the 72 hour enzymatic hydrolysis*** (10% glucan loading)* of the water insoluble cellulosic component of steam pretreated and subsequently alkaline peroxide treated wheat straw (expressed as g per 100 g substrate**)

| | Xylose yield |
|---|---|
| Hot water washed wheat straw | 6.1 (0.0) |
| Hot water washed wheat straw + Tween 80 | 6.3 (0.2) |
| Alkaline peroxide treated wheat straw | 5.8 (0.0) |
| Alkaline peroxide treated wheat straw + Tween 80 | 6.0 (0.1) |

TABLE 9

Dissolved solids present in the 72 hour enzymatic hydrolysate of steam pretreated and subsequently alkaline peroxide treated wheat straw (% wt/wt)

|  | Dissolved Solids (% wt/wt) |
| --- | --- |
| Hot water washed wheat straw | 13.8 (0.1) |
| Hot water washed wheat straw + Tween 80 | 12.3 (0.0) |
| Alkaline peroxide treated wheat straw | 14.1 (0.2) |
| Alkaline peroxide treated wheat straw + Tween 80 | 13.9 (0.1) |

Further investigations of the enzymatic hydrolysis of steam treated and subsequently alkaline peroxide treated wheat straw with the addition of a surfactant (Tween 80) were performed as set out in Tables 10-12.

TABLE 10

Monomeric glucose yield during the fed-batch enzymatic hydrolysis (10% glucan loading)* of the water insoluble cellulosic component of steam pretreated and subsequently alkaline peroxide treated wheat straw with the addition of Tween 80 (expressed as g per 100 g total glucan**).

|  | After first 36 Hours | After next 24 hours | After next 24 Hours | After next 24 Hours |
| --- | --- | --- | --- | --- |
| Glucose yield** | 93.4 (0.5)*** | 72.7 (1.3) | 61.5 (0.7) | 49.7 (2.8) |
| Dissolved solids | 12.9 (0.1) | 10.0 (0.1) | 8.4 (0.0) | 6.9 (0.3) |

*13.3% solids loading for peroxide treated substrate to obtain 10% glucan loading. 0.2% Tween 80 in the reaction mixture only in the beginning. Cellulase loading: 31 mg protein (CTec 2) per g of glucan and 3.1 mg/g glucan before adding every fresh batch of the substrates.
**100 g glucan should theoretically release ~110 g glucose.
****Values in the bracket represent standard deviations

TABLE 11

Monomeric xylose yield during the fed-batch enzymatic hydrolysis (10% glucan loading) of the water insoluble cellulosic component of steam pretreated and subsequently alkaline peroxide treated wheat straw expressed as g per 100 g total substrate used for hydrolysis in every stage).

| After first 36 hours of enzymatic hydrolysis | 5.5 (0.1) |
| --- | --- |
| After next 24 hours | 4.3 (0.0) |
| After next 24 hours | 3.6 (0.1) |
| After next 24 hours | 2.9 (0.0) |

TABLE 12

Fraction of the total protein present in the supernatant prior to the addition of every batch of fresh substrates and enzymes (expressed as % of the total protein added**).

|  | Fed batch hydrolysis* | | | | Batch hydrolysis** |
| --- | --- | --- | --- | --- | --- |
|  | After first 36 hours | After the next 24 hour | After the next 24 hour | After the next 24 hours | At the end of 72 hours |
| Fraction of the total proteins in the liquid | 61.6 (1.1) | 63.3 (0.5) | 63.1 (1.7) | 66.2 (2.4) | 72.7 (2.8) |

*31.1 mg protein loading/g cellulose in the beginning of first batch of hydrolysis and 3.1 mg protein/g cellulose before the addition of every fresh batch of substrates. 10% glucan consistency in the first 36 hours followed by the addition of 10% glucan in every subsequent 24 hours.
**Protein loading: 31.1 mg/g cellulose & 10% glucan consistency Example 5

A cellulosic glucose product produced by the activation and enzymatic conversion methods described herein was prepared and was deteremined to have the following specifications:
Chemical and Physical Data
Total solids 50-70%
Moisture 30-50%
Composition (dry matter basis):

| Glucose | 95% |
| --- | --- |
| Xylose | 4% |
| Xylo-oligosaccharides | 1% |
| Ash | <0.01% |
| pH: | 3-5 |
| Conductivity: | (30% DS) 50 μs/cm |
| Specific gravity: | 1.2 |
| Appearance: | clear solution |
| Odor: | sweet |

Mineral Ash Content (PPM)

| Chloride | 16 |
| --- | --- |
| Sulphate | <1 |
| Calcium | 5 |
| Potassium | <1 |
| Magnesium | <1 |
| Sodium | 2 |
| Phosphorous | 2 |

Glycemic Index Data

The cellulosic glucose product having the composition described above was found to have a glycemic index (GI) of 72. By comparison glucose alone is known to have a glycemic index of 100. Dextrose is also known to have a glycemic index of 100 while maltose and maltodextrin are known to have glycemic indexes of 105 and 110 respectively.

The present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A method for producing a glucose-rich sugar stream from activated cellulose, the method comprising subjecting activated cellulose to enzymatic hydrolysis with one or more cellulase enzymes, a surfactant and polyaspartic acid to produce the glucose-rich sugar stream.

2. The method of claim 1, wherein the one or more cellulase enzymes are selected to hydrolyse 1,4-beta-D-glycosidic linkages into monosaccharides.

3. The method of claim 1, wherein the polyaspartic acid has a molecular weight between 500 and 10,000.

4. The method of claim 1, wherein the polyaspartic acid is present at a loading of less than 2% of the weight of the cellulose content of the activated cellulose.

5. The method of claim 4, wherein the polyaspartic acid is present at a loading of less than 0.1% of the weight of the cellulose content of the activated cellulose.

6. The method of claim 1, wherein the surfactant is a non-ionic surfactant.

7. The method of claim 1, wherein the one or more cellulase enzymes forms a ternary complex with the surfactant and the polyaspartic acid.

8. The method of claim 1, wherein the one or more cellulase enzymes are present at a loading of 0.1 to 5 mg enzyme protein per g glucan.

9. The method of claim 8, wherein the one or more cellulase enzymes are present at 2 to 60 FPU/g glucan.

10. The method of claim 1, comprising subjecting the activated cellulose to enzymatic hydrolysis for between 24 and 144 hours.

11. The method of claim 1, further comprising subjecting the glucose-rich sugar stream to an enzyme removal treatment and obtaining a glucose-rich and enzyme poor sugar stream and an enzyme recycle stream, recycling the enzyme recycle stream to the enzymatic hydrolysis.

12. The method of claim 11, wherein subsequent to introducing the enzyme recycle stream to the enzymatic hydrolysis, the method produces a yield of glucose that is greater than about 70%.

13. The method of claim 12, wherein the method produces a yield of glucose that is greater than about 90%.

14. The method of claim 11, wherein the enzyme removal treatment comprises:
  (a) contacting the glucose-rich sugar stream with cellulose and obtaining cellulose with enzymes absorbed thereon; and,
  (b) subjecting the glucose-rich sugar stream to a cellulose removal step to obtain the glucose-rich and enzyme poor sugar stream which has a reduced level of cellulose and the enzyme recycle stream which has the cellulose with the enzymes absorbed thereon.

15. The method of claim 1, wherein the glucose-rich sugar stream comprises greater than about 12% glucose.

16. The method of claim 15, wherein the glucose rich sugar stream comprises greater than about 16% glucose.

17. The method of claim 1, wherein the yield of glucose is greater than about 70%.

18. The method of claim 17, wherein the yield of glucose is greater than about 90%.

19. The method of claim 1, comprising subjecting the activated cellulose to enzymatic hydrolysis for less than 48 hours.

20. A method for producing a glucose-rich sugar stream, the method comprising:
  (a) providing activated cellulose comprising a mix of cellulose II, hydrated cellulose II and alkali-cellulose IV;
  (b) subjecting the activated cellulose to enzymatic hydrolysis with one or more cellulase enzymes, a surfactant and polyaspartic acid to produce the glucose-rich sugar stream.

21. The method of claim 20, wherein the activated cellulose is produced by a two-step method for activating a cellulosic feedstock comprising:
  (a) subjecting the feedstock to a first activation step wherein the feedstock is treated at a temperature greater than 190° C. and a pressure greater than 200 psig to produce a first activated cellulose stream comprising cellulose II and insoluble solids; and
  (b) subjecting the first activated cellulose stream to a second activation step wherein the first activated cellulose stream is treated with an alkali at a lower temperature than the first activation step to produce a second activated cellulose stream comprising cellulose IV.

22. The method of claim 20, further comprising subjecting the glucose-rich sugar stream to an enzyme removal treatment and obtaining a glucose-rich and enzyme poor sugar stream and an enzyme recycle stream.

23. The method of claim 20, wherein the glucose-rich sugar stream comprises greater than about 12% glucose.

24. The method of claim 23, wherein the glucose-rich sugar stream comprises greater than about 16% glucose.

25. The method of claim 20, wherein the yield of glucose is greater than about 70%.

26. The method of claim 25, wherein the yield of glucose is greater than about 90%.

* * * * *